United States Patent
Silverman et al.

[11] Patent Number: 5,931,865
[45] Date of Patent: Aug. 3, 1999

[54] MULTIPLE-LAYERED LEAK RESISTANT TUBE

[75] Inventors: James Silverman; Bret Kilgrow, both of Flagstaff, Ariz.

[73] Assignee: Gore Enterprise Holdings, Inc., Newark, Del.

[21] Appl. No.: 08/977,465

[22] Filed: Nov. 24, 1997

[51] Int. Cl.[6] ........................................................ A61F 2/06
[52] U.S. Cl. .............................................. 623/1; 604/264
[58] Field of Search .................... 604/73, 264, 523–524, 604/244; 600/36; 623/1, 11, 12; 138/137, 140

[56] References Cited

U.S. PATENT DOCUMENTS

| | | | |
|---|---|---|---|
| 3,566,868 | 3/1971 | Baptist et al. | 128/214 |
| 3,814,137 | 6/1974 | Martinez | 138/103 |
| 3,953,566 | 4/1976 | Gore | 264/288 |
| 4,076,023 | 2/1978 | Martinez | 128/214 R |
| 4,084,266 | 4/1978 | Poirier | 3/1 |
| 4,130,904 | 12/1978 | Whalen | 3/1.4 |
| 4,184,489 | 1/1980 | Burd | 128/214 R |
| 4,187,390 | 2/1980 | Gore | 174/102 R |
| 4,323,525 | 4/1982 | Bornat | 264/24 |
| 4,416,028 | 11/1983 | Eriksson et al. | 3/1.4 |
| 4,474,630 | 10/1984 | Planck | 156/62.4 |
| 4,475,972 | 10/1984 | Wong | 156/167 |
| 4,619,641 | 10/1986 | Schanzer | 604/8 |
| 4,632,842 | 12/1986 | Karwoski et al. | 427/2 |
| 4,652,263 | 3/1987 | Herweck et al. | 623/1 |
| 4,718,907 | 1/1988 | Karwoski et al. | 623/12 |
| 4,738,740 | 4/1988 | Piuchuk et al. | 154/167 |
| 4,743,250 | 5/1988 | Kitagawa et al. | 623/1 |
| 4,743,251 | 5/1988 | Barra | 623/1 |
| 4,850,999 | 7/1989 | Bittmann et al. | 623/1 |
| 4,875,468 | 10/1989 | Krauter et al. | 128/3 |
| 4,877,661 | 10/1989 | House et al. | 428/34.9 |
| 4,878,908 | 11/1989 | Martin et al. | 623/1 |
| 4,932,964 | 6/1990 | Bittmann et al. | 623/1 |
| 4,955,899 | 9/1990 | Della Corna et al. | 623/1 |
| 4,969,896 | 11/1990 | Shors | 623/1 |
| 4,986,832 | 1/1991 | Kaneko et al. | 623/1 |
| 5,024,671 | 6/1991 | Tu et al. | 623/1 |
| 5,026,513 | 6/1991 | House et al. | 264/127 |
| 5,061,276 | 10/1991 | Tu et al. | 623/1 |
| 5,100,422 | 3/1992 | Berguer et al. | 606/151 |
| 5,116,360 | 5/1992 | Pinchuk et al. | 623/1 |
| 5,176,653 | 1/1993 | Metais | 604/167 |
| 5,192,310 | 3/1993 | Herweck et al. | 623/1 |
| 5,246,452 | 9/1993 | Sinnott | 623/1 |
| 5,545,212 | 8/1996 | Wakabayashi et al. | 623/1 |
| 5,549,664 | 8/1996 | Hirata et al. | 623/1 |
| 5,628,782 | 5/1997 | Myers et al. | 623/1 |
| 5,716,395 | 2/1998 | Myers et al. | 623/1 |
| 5,800,512 | 9/1998 | Lentz et al. | 623/12 |
| 5,814,405 | 9/1998 | Branca et al. | 428/311.51 |
| 5,861,033 | 1/1999 | Martakos et al. | 623/11 |

FOREIGN PATENT DOCUMENTS

| | | |
|---|---|---|
| 0 047 231 A2 | 3/1982 | European Pat. Off. |
| 0 117 072 A1 | 6/1984 | European Pat. Off. |
| 0 160 483 A2 | 11/1985 | European Pat. Off. |
| 0 407 692 A1 | 1/1991 | European Pat. Off. |
| 6-343688 | 12/1994 | Japan. |
| 2 015 118 | 9/1979 | United Kingdom. |
| 2 092 894 | 8/1982 | United Kingdom. |
| 82/01647 | 5/1982 | WIPO. |
| 97/07751 | 3/1997 | WIPO. |

OTHER PUBLICATIONS

Brochure: GORE–TEX Vascular Grafts for Hemodialysis: Techniques for the Care and Cannulation of A–V Grafts. W.L. Gore & Associates, Inc., Sep. 1997.

*Primary Examiner*—Corrine McDermott
*Assistant Examiner*—Cris L. Rodriguez
*Attorney, Agent, or Firm*—David J. Johns

[57] ABSTRACT

The present invention is an improved tubular device for carrying liquids or gases that is resistant to leakage following a puncture. In its preferred form, the tubular device employs two or more concentrically mounted tube elements that are adapted to move relative to one another following puncture and removal of the puncturing device. This relative movement creates a discontinuous opening through the device that is resistant to fluid leakage. The device may likewise be constructed to cause at least one of the puncture holes to contract, thus further limiting fluid loss. The device of the present invention is particularly useful as an implantable device, such as a vascular graft.

23 Claims, 4 Drawing Sheets

MULTIPLE-LAYERED LEAK RESISTANT TUBE

BACKGROUND OF THE INVENTION

1. Field of the Invention

The present invention relates to tubular structures, such as vascular grafts and the like, that are adapted to carry a fluid stream, and particularly to tubular structures that are resistant to leakage following a puncture.

2. Description of Related Art

Tubular structures are used to carry a variety of fluid streams, including both liquids and gases. It is desirable for many of these tubular structures to be resistant to punctures, either accidental or intentional, and/or to provide some degree of self-healing following a puncture so as to minimize fluid leakage.

Of particular interest to the present inventors is the possibility of creating a tubular structure for carrying blood or other body fluids that will provide improved self-healing characteristics. For instance, in the instance of vascular grafts, these devices often must be punctured both in initial installation (for example, while being sutured in place) and in subsequent medical procedures (for example, to provide an injection, to place a catheter, or the like). As a result, it is highly desirable that blood loss is minimized after each puncture through such tubes.

Even more critical is when vascular grafts are used as an access site for dialysis and the like. In the case of an arterial-venous ("AV") access graft, these vascular grafts must withstand several punctures a week over the life of the graft. This is a highly demanding environment that inevitably leads to graft failures due to excessive numbers of puncture holes, often requiring installation of two or more grafts over the course of a year. Unfortunately, each new AV access graft generally will not function properly until it has achieved tissue in-growth in a patient, a process that can take weeks after installation to occur adequately. Puncture of these tubes ("cannulation") before full tissue in-growth may result in excessive subcutaneous bleeding and serious complications.

A number of solutions have been proposed to reduce tubular leakage following punctures. For example, in U.S. Pat. 4,184,489 to Martinez it is proposed to use two concentric elastomeric sleeves, with the outer sleeve sized to radially compress the inner sleeve. This construction is reported to improve the sealing of the device following puncture. Similarly, in U.S. Pat. 4,184,489 to Burd it is taught to surround a blood conduit tube with an elastomeric sleeve and then a C-shaped needle-impenetrable member partially surrounding the sleeve. This device is again asserted to prevent leakage into and out of the tube during and after needle penetration by maintaining a radial compression on the tube.

A number of other devices teach employing two or more layers of different materials to achieve some degree of puncture hole contraction following removal of the puncture device. For example, in U.S. Pat. No. 4,619,641 to Schanzer it is proposed to employ two concentric expanded polytetrafluoroethylene (PTFE) tubes having a gap between them and then filling the gap with a silicone adhesive layer. Comparing the performance of this device with a device having the same two expanded PTFE tubes and no silicone layer filling the gap between them, Schanzer reports significantly reduced blood loss with the three layered PTFE-silicone-PTFE hemoaccess tube.

While these various devices may provide some improvement in leakage protection over puncturing through a single layer tube, they work on a similar principle that the puncture hole should be constrained with an elastomer or similar material so that it will more quickly contract to reduce leakage upon removal of a needle. There are a number of serious drawbacks with this approach. First, these elastomer tubes tend to have poor handling characteristics, with some surgeons referring to them as "rubber hoses" because they bend and handle so poorly. Second, these tubes generally do not sew in place well, again making them difficult for surgeons to handle and install. Third, these tubes tend to be difficult to "revise" if a blockage occurs in them. Finally, since these tubes rely only on the elastic qualities of the tube wall to seal holes, there will always remain a hole all the way through the wall of the device following needle removal. Even with rapid contraction around the hole, some leakage through the hole after needle removal will be expected to occur. Additionally, the presence of a continuous hole through the wall of the device also is believed to compromise device integrity over time.

Another problem with multiple layered devices is that size is often a constraint in creating any implantable device. Most implantable devices must be as small as possible since space is almost always quite limited. Unfortunately, most of the devices that reduce leakage rely on an increased in the bulk of wall layers to accomplish rapid hole reduction (that is, by increasing the thickness of the wall layers by laminating together multiple layers or simply using thicker wall material). This inevitably leads to a compromise between effective leakage reduction and the total acceptable size of the device.

Finally, many of these previous devices require use of less than preferred implantable materials. While PTFE is a preferred artificial material for implantation, since it is highly bio-compatible, it has rather poor recovery properties following puncture. As a result, prior devices have employed other materials to aid in quickly reducing hole size, such as silicone or other elastomeric materials. This creates devices that have better elastic properties, but with possibly less than ideal bio-compatibility.

Accordingly, without intending to limit or define the scope of the present invention with the following purposes, the present invention addresses deficiencies found in prior devices. First, it is a primary purpose of the present invention to create a tubular structure that exhibits limited leakage following puncture.

It is still another purpose of the present invention to provide a reduced-leakage tubular structure that incorporates reduced leakage properties with minimal increased space requirements.

It is a further purpose of the present invention to provide a reduced-leakage tubular structure that can be constructed substantially from highly biocompatible material, such as PTFE.

These and other purposes of the present invention will become evident from review of the following specification.

SUMMARY OF THE INVENTION

The present invention comprises a tubular device that is resistant to leakage when punctured. The device of the present invention employs a first tube element at least partially covered with a second element that is adapted to move relative to the first tube element when the device is punctured diagonally with a needle. The device is constructed so that misaligned holes will be left through the device when the needle is removed, thus reducing leakage through the device.

Most preferred, a first tube element and a second tube element are mounted concentrically with one another and have an interference fit therebetween. The interference fit assures that tensions or stresses applied to either or both of the tube elements will remain resident within the device in use. The tube elements are adapted to move relative to one another when punctured. By maintaining different stresses on the tube elements, the result is that relative movement will more readily occur between the tube elements during and after a puncture, assuring hole misalignment following needle removal.

This misalignment of openings vastly decreases fluid leakage from the device following a puncture. Additionally, the device can be constructed to provide self-healing properties by providing one of the tube elements with a compressive stress, causing the opening in it to close-up following needle removal.

The device of the present invention is believed to have a variety of useful applications, but is particularly intended for use as an implantable device, such as a vascular graft and particularly to an AV access graft. In fact, the device of the present application is believed to be beneficially employed as an early cannulation vascular access graft.

As an implantable device, the present invention can be constructed from highly bio-compatible materials, such as polytetrafluoroethylene, without the need to introduce elastomeric materials, such as silicone, which are less desirable in implantable devices. Additionally, the leak resistant properties of the present invention are achieved with little increase in the dimension of the final product, again making it especially suitable for implantation within the tight confines of a body.

DESCRIPTION OF THE DRAWINGS

The operation of the present invention should become apparent from the following description when considered in conjunction with the accompanying drawings, in which.

DETAILED DESCRIPTION OF THE INVENTION

The present invention is an improved tubular device that is resistant to leakage following a puncture with a needle and subsequent removal of the needle. As the term "needle" is used herein it is intended to include any object that can cause and/or maintain a puncture hole in the tubular device of the present invention, including without limitation: a pin or sewing needle; a hypodermic needle; a catheter device; a cannula device; a scalpel or knife; a thorn or other sharp, pointy object; et cetera.

Figure 1:
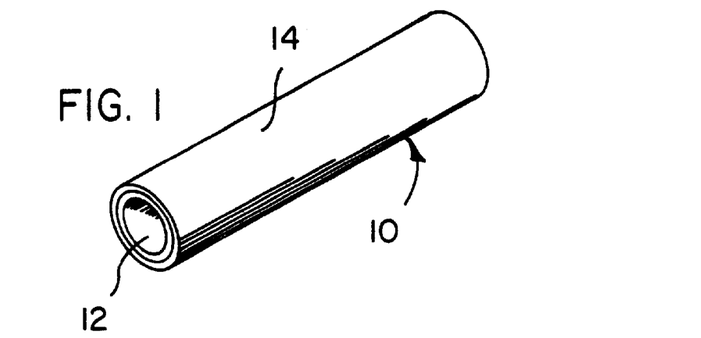
FIG. 1 is a three-quarter isometric view of one embodiment of a tubular device of the present invention.
Figures 2, 3:
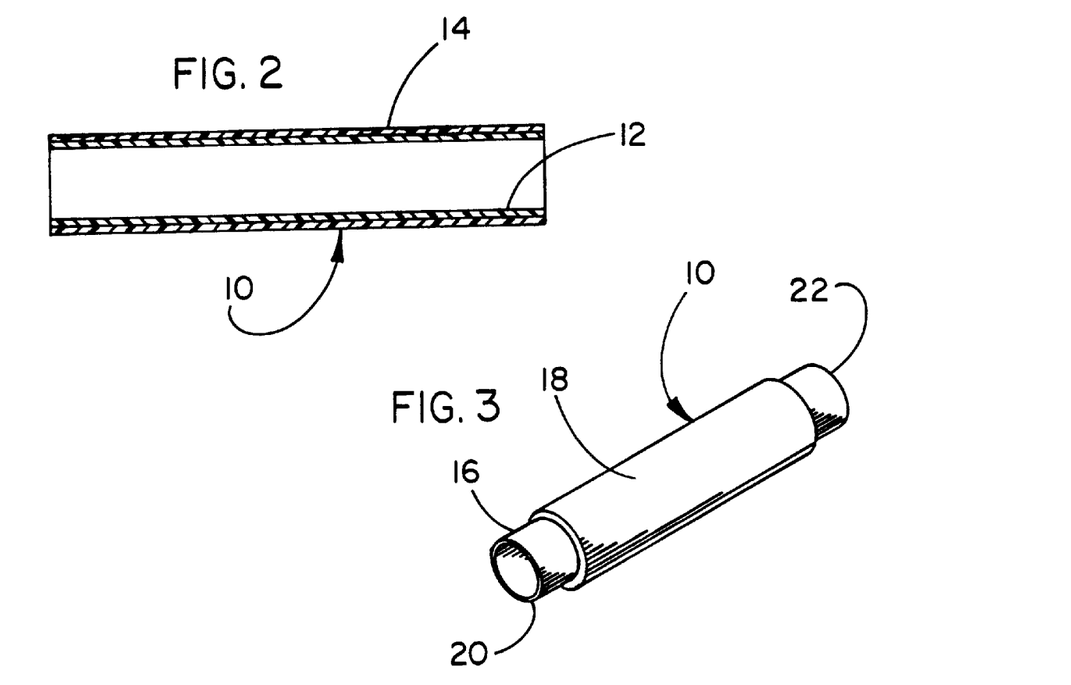
FIG. 2 is a cross-section view of the device of FIG. 1.
FIG. 3 is a three-quarter isometric view of another embodiment of a tubular device of the present invention.

The tubular device of the present invention is particularly intended for use as an implantable device, such as a vascular graft, that is capable of transferring body fluids. The device of the present invention is especially useful as an AV access graft or the like. Especially preferred is use of the device of the present invention to allow for "early cannulation," whereby the device may be safely punctured with minimal leakage soon after implantation without the need to wait for device in-growth. It should be appreciated, however, that the device of the present invention may have numerous other applications wherein a tubular device carrying a fluid must be resistant to leakage following a puncture. Examples of other possible applications include: a tube adapted for sampling from a fluid stream, such as in laboratory analysis equipment; a self-healing tube or bag for carrying a liquid or pressurized gas, such as in a hose, shock absorber, tire inner tube, sample bag, etc.; a filter bag; chemical transport bladders; et cetera. FIGS. 1 and 2 illustrate one embodiment of a tubular device 10 of the present invention. The device 10 comprises at least a first tube element 12 and a second element 14, preferably tubular, each mounted concentrically with one another and having an "interference fit," with one another.

The term "interference fit" as used herein connotes a sufficiently tight contact between the tube elements, at least when the device 10 is installed in place and under normal operating pressures, so that a longitudinal stress applied to one of the tube elements will be maintained. For example, if the first tube element is stretched longitudinally (that is, has a positive stress applied along its length) and an interference fit is established with the second element, then the first tube element will retain at least some of its stretched orientation due to the tight fit between the first tube element and the second element. It should be evident that to whatever degree the first tube element may contract from its stretched dimensions in this example, the second element will then be compressed to that degree (that is, the second element will have a negative stress applied along its length).

It is preferred that the second element is tubular, providing a ready means for forming a snug fit between the first tube element and the second element. However, as is explained in greater detail below, the second element may alternatively comprise a strip or other configuration of material that is attached to the first tube element in such a way as to allow relative movement between the first tube element and the second element.

When two tubular elements are employed, the interference fit employed with the present invention is preferably sufficiently tight to maintain a stress differential between the tube elements, as will become clear from the following description. It is most important, however, that the interference fit between the tube elements allows for the relative movement between the tube elements during and after a diagonal puncture. Thus, it is not desired to have a fit that is so tight that at least portions of the tube elements cannot slide longitudinally with respect to each other. On the other hand, it is likewise not desirable to have a fit between the tubes that is so loose that significant liquid leakage can occur in the space between the tubes.

In the preferred embodiment of the present invention, at least two tube elements 12, 14 are employed and each of the elements 12, 14 should have a stress applied and maintained along its length, with the longitudinal stress applied to the first tube element 12 being different from the longitudinal stress applied to the second tube element 14. For example, the first tube element may have a positive stress applied along its length (that is, it is stretched longitudinally), with the second tube element having no stress (that is, it maintains its natural resting state of stress) or a negative stress applied along its length (that is, it is compressed longitudinally). Conversely, the second tube element may have a positive stress applied along its length, with the first tube element having no stress or a negative stress applied along its length. The important aspect is that a stress differential is established between the tube elements so that they will each react differently when a puncture is applied through the device.

By way of example, a vascular graft having a 7 mm final outer diameter and 5.8 mm final inner diameter can be constructed from two tubes of expanded polytetrafluoroethylene (PTFE), a first tube having an initial inner diameter of about 6 mm, an outer diameter of about 7.2 mm, a wall thickness of about 0.6 mm, and an initial length of about 30 cm, and a second tube having an initial inner diameter of about 6 mm, an initial outer diameter of about 6.9 mm, a wall thickness of about 0.45 mm, and an initial length of about 50 cm. These two tubes can be mounted coaxially with one another and will establish an interference fit between each other.

In this instance a longitudinal stress differential can be established between the two expanded PTFE tubes by applying a longitudinal tensile strain to the first tube, and applying a longitudinal compressive strain to the second tube to reduce its length to about 70% of its original length. In this instance, when the two tubes are released from their strain and constraint, the first tube will slightly recover, with the second tube undergoing some degree of compression. In this unrestrained state, the first tube will have a tensile strain applied along its length of about 30% (that is, it is about 30% longer than its initial length) and the second tube will have a compressive strain applied along its length of about 60% (that is, it is about 60% of its initial length).

These properties can also be expressed by the degree of compression applied to each of the tubes. By placing at least two measured marks on each of the tubes in their resting states, the degree of stretch or compression between the two tubes can be measured by the amount of change in distance between the pre-measured marks on the two tubes. For example, a first set of marks may be placed on a first tube 1 cm apart longitudinally and a second set of marks may be place on a second tube 1 cm apart longitudinally. When the two tubes are attached together with an interference fit and a stress differential place on the tubes, then the distance between the marks in either the first set of marks or the second set of marks will be either increased or decreased. In fact, for most applications it would be expected that expansion of one tube during construction will create some degree of compression in the other tube in the final device, thus causing the distance between both sets of marks to change.

Using these criteria, for vascular access applications it is believed desirable to have at least a 50 to 70% compression on one of the tubes in the completed device, with a preferred compression of about 55 to 65%. In the instance of tubes with 1 cm marks on them, this means that following placing the tubes together the two marks on the compressed tube will be approximately 0.4 to 0.6 cm apart, and more preferably 0.45 to 0.55 cm apart. A differential in tension between the two tubes (that is, one tube under compression and the other tube under stretch) might result in the compressed tube having marks 0.5 to 0.7 cm apart and the stretched tube having marks 1.2 to 1.4 cm apart.

When considering a completed device of the present invention the relative stresses applied to the tube elements may be measured by applying the same principles in reverse. For example, measured sets of marks may be placed on the inside and outside tubes of the complete device and then the device may be disassembled, relieving any stress differential on the tubes. Any change in the distance between the measured marks may then be measured to provide the degree of change. For example, a vascular graft having two tubes with an interference fit between them may have sets of 1 cm marks placed on both the inside tube and the outside tube. Once disassembled, stress differential between the tubes will be relieved, which will either lengthen or shorten the distance between the marks in each set. A change of distance from 1 cm to about 1.67 cm on one of the tubes will indicate a degree of compression of about 60%. Using this method, one can readily determine whether a multiple layered tube has stress differentials between its various tube elements.

Alternatively, a stress differential can be confirmed by performing a simple puncture test on a device of the present invention. As is illustrated in FIGS. 5 through 9 and is explained in detail below, when a diagonal puncture is placed through the device 10 with a needle, a stress differential between the layers will cause the two layers of the device to move relative to each other when the needle is removed, creating a discontinuous hole through the device. Thus a stress differential between the tube elements can also be shown through this simple puncture test.

It should be appreciated that the present invention will also function by using materials with different moduli of elasticity for the first tube element and the second element. In this manner, each of the layers will react differently to a diagonal puncture, again causing a hole misalignment when the needle is removed. A further refinement of the present invention employs materials with different moduli of elasticity and a stress differential applied to each of the layers.

Figure 4:
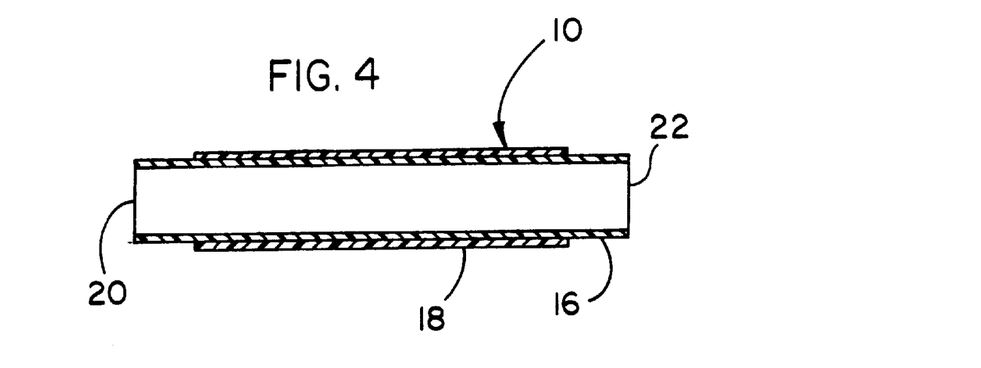
FIG. 4 is a cross-section view of the device of FIG. 3.

An alternative embodiment of a device 10 of the present invention is illustrated in FIGS. 3 and 4. In this embodiment a first tube element 16 is employed that is longer in length than the second tube element 18. Again, the two tube elements 16, 18 should have an interference fit established between them and a stress differential between the two elements 16, 18. The device of this embodiment is intended to address those instances where the device as a whole does not need to be cannulated, but only that segment corresponding to the length of the second tube element 18.

Again, the stresses applied to each of the two tube elements 16, 18 may be positive, none, or negative, so long as a stress differential is established. As used herein, the term "tensile stress" refers to a longitudinal positive "pull" on the tube component; the term "compressive stress" refers to a negative compression of the tube component. Since the anchorage of this device will be through attachment of the first tube element 16 at its ends 20, 22, then it is believed to be preferred to have a tensile stress applied along the first tube element 16.

The operation of the present invention is illustrated in FIGS. 5 through 9. As is shown, a wall segment 24 of the device 10 is shown comprising an inner or first tube element 26 and an outer or second tube element 28. In this embodiment, the first tube element 26 is the one with a positive stress along its length.

Figure 5:
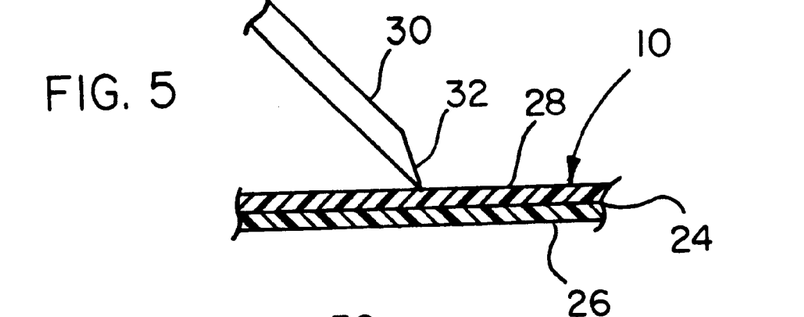
FIG. 5 is an enlarged cross-section view of a wall segment of a device of the present invention, showing a needle preparing to enter the device.
Figure 6:
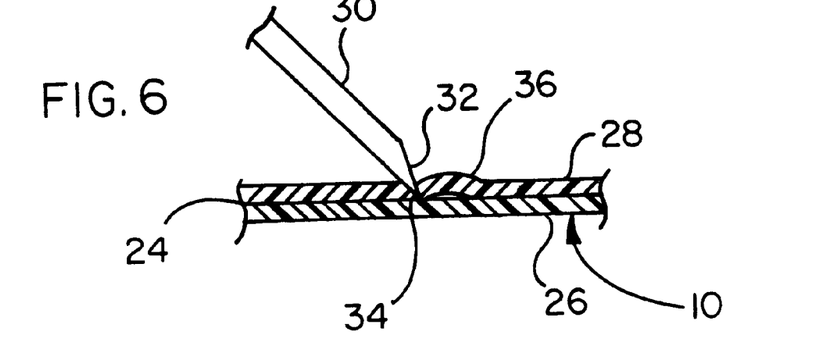
FIG. 6 is the enlarged cross-section view of FIG. 5, with the needle having penetrated an outer layer of the device.
Figure 7:
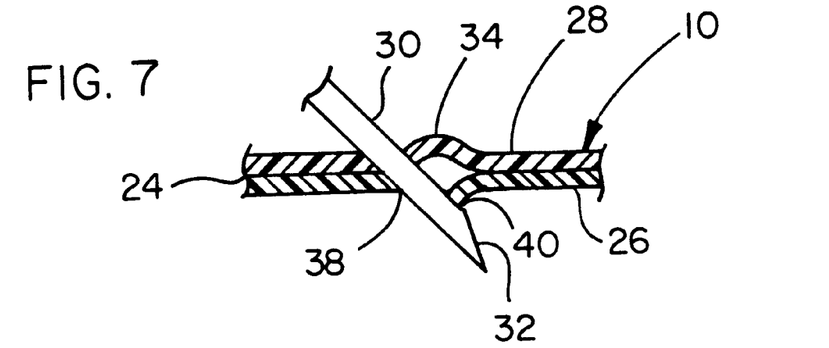
FIG. 7 is the enlarged cross-section view of FIG. 5, with the needle having entered both the outer layer and an inner layer of the device.

A needle 30 is shown in FIGS. 5 through 7, in this instance a 15 gauge hypodermic needle having a cutting tip 32. The needle 30 is oriented at a diagonal to the wall segment 24 (that is, it is positioned at an angle other than directly perpendicular to the wall segment). Normally a needle of this type will be introduced diagonally at an angle of about 15 to 60 degrees from perpendicular, with an angle of about 45 degrees from perpendicular illustrated.

Shown in FIG. 6 is the needle 30 after it has penetrated the second tube element 28 forming a first opening 34. As can be seen, since the two tube elements are attached together with an interference fit that allows for relative movement between the two tube elements 26, 28, the second tube element 28 undergoes some initial movement, shown as a slight bulge 36.

FIG. 7 illustrates the needle 30 after it has penetrated both the second tube element 28 and the first tube element 26 to form a second opening 38. As can be seen, the first tube element 26 also undergoes relative movement, in this instance a downward distortion 40.

Figure 8:
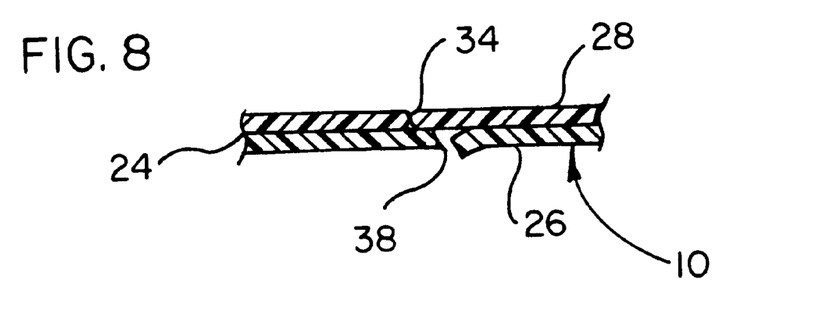
FIG. 8 is the enlarged cross-section view of FIG. 5, with the needle having been removed from the device and illustrating the discontinuous nature of the openings left in the device through the outer and inner layers.
Figure 9:
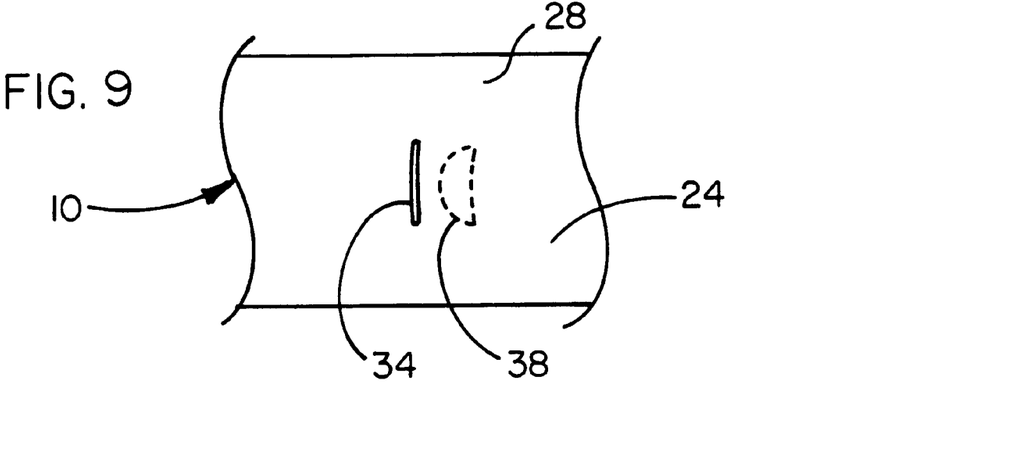
FIG. 9 is a top plan view of the wall segment of the device of the present invention shown in FIG. 8, showing the opening in the outer layer and showing in phantom the discontinuous opening in the inner layer.

As is shown in FIGS. 8 and 9, once the needle is removed, the relative stresses on the first tube element 26 and the second tube element 28 cause them to return to different resting states. As a result, the first opening 34 and the second opening 36 do not align with one another. This separation of the two openings 34, 36 is referred to herein as being a "misalignment" of the openings or "discontinuous opening" through the wall segment 24. Since a continuous opening is not left in the wall, this vastly decreases the amount and duration of fluid that will pass through the wall following needle removal. Additionally, while the first tube element 26 is under tensile stress, causing the second opening 36 to be somewhat enlarged, the second tube element 28 is actually under a compressive stress, causing the first opening 34 to close up, thus further limiting the amount and duration of fluid that will escape the device.

For use as an implantable device, it is preferred that the present invention be constructed from materials suitable for implantation, and especially bio-compatible material or materials, such as polytetrafluoroethylene (PTFE), expanded PTFE, DACRON® polymer, polyurethane, silicone elastomer, and the like.

Particularly preferred is a device constructed from expanded PTFE, such as that disclosed in U.S. Pat. Nos. 3,953,566, 3,962,153, 4,096,227, and 4,187,390, each incorporated by reference. Tubes made in accordance with these patents adapted for use as a vascular graft are commercially available from W. L. Gore & Associates, Inc., Flagstaff, Ariz., under the trademark GORE-TEX®.

In particular, a device of the present invention can be constructed by combining commercially available vascular grafts in the following manner. A Stretch GORE-TEX® Vascular Graft may be used as a base graft. These stretch grafts are available from W. L. Gore & Associates, Inc., in a variety of internal diameters (ranging from about 5 to 10 cm) and a nominal wall thickness of about 0.6 mm. The base graft is placed onto an assembly mandrel and secured at one end. A load is placed on the opposite end to apply tension to the graft.

A second GORE-TEX® vascular graft may be used as the outer graft, preferably one having a relatively thin wall. Thin wall vascular grafts are available from W. L. Gore & Associates, Inc., in a variety of internal diameters (ranging from about 3 to 10 cm) and a nominal wall thickness of about 0.45 mm. The second vascular graft should be sized to be approximately the same internal diameter as that of the base graft, thus forming an interference fit when the two grafts are combined together.

The second vascular graft is pulled over the base graft and the assembly mandrel creating an interference fit between the two grafts. The outer graft is then longitudinally compressed along its length. The outer graft may be compressed from about 50 to 70% of its original length, with a compression of about 60% being most preferred. This provides longitudinal compression in the outer graft. The combined grafts are then removed from the assembly mandrel. In use, longitudinal forces applied to the graft will be applied to the base graft so that the outer graft will remain in compression.

It should be evident that two, three, or more grafts may be combined in this manner, with compression or tension applied to one or more of the layers to support relative movement between the graft layers during and after a puncture.

It should be further evident from the above description that the present invention solves many of the prior deficiencies with leak-resistant tubular devices. First, the combination of discontinuous openings through the device wall and the negative stress on one of the tube elements, causing the tube to "close up," combine to provide a device that is very resistant to leakage. Second, the device can be constructed from very few components and in dimensions that are similar to those of conventional single wall tubes. As a result, the device of the present invention is very compact and requires little or no additional space for use over more conventional vascular grafts and similar products. Third, the device of the present invention can be constructed substantially or even entirely from highly bio-compatible material, such as PTFE, without the need to introduce elastomers or other products that might cause compatibility problems or other complications.

Figure 10:
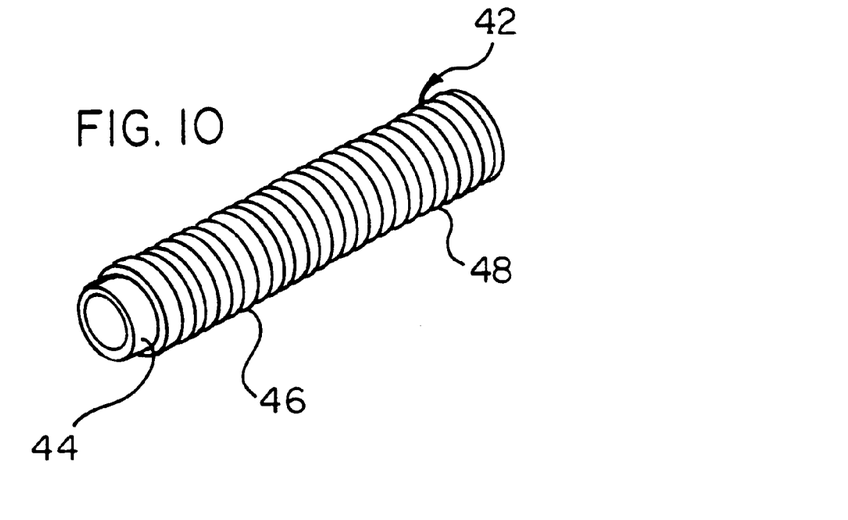
FIG. 10 is a three-quarter isometric view of another embodiment of a device of the present invention, this embodiment comprising a base tube covered with a tape-wrapped second tube.
Figure 11:
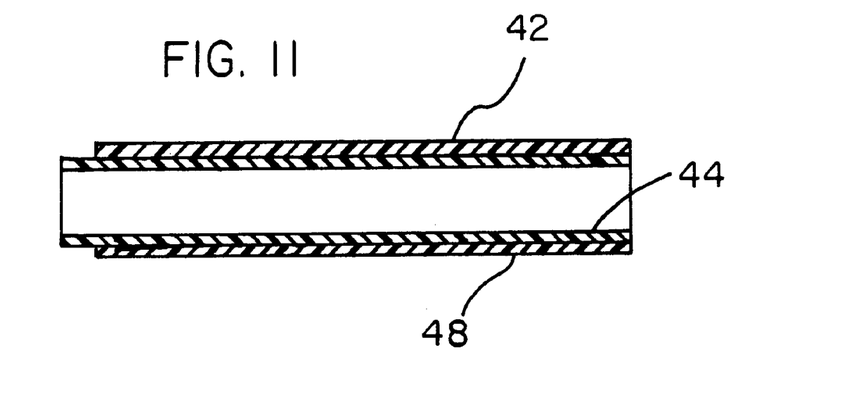
FIG. 11 is a longitudinal cross-section of the device of FIG. 10.

For other applications, the device of the present invention can be constructed from a wide variety of materials and in a variety of different constructions. For instance, FIGS. 10 and 11 illustrate a two-layer construction of a leak-resistant tube 42 of the present invention. In this embodiment, a continuous base tube 44 is covered with an outer layer of a helically wound tape 46, thus creating the outer tubular element 48. Once again, by applying either tension or compression on the base tube 44 during the wrapping process, the outer tubular element 48 will retain the differential stress within the device 42.

Figures 12, 13:
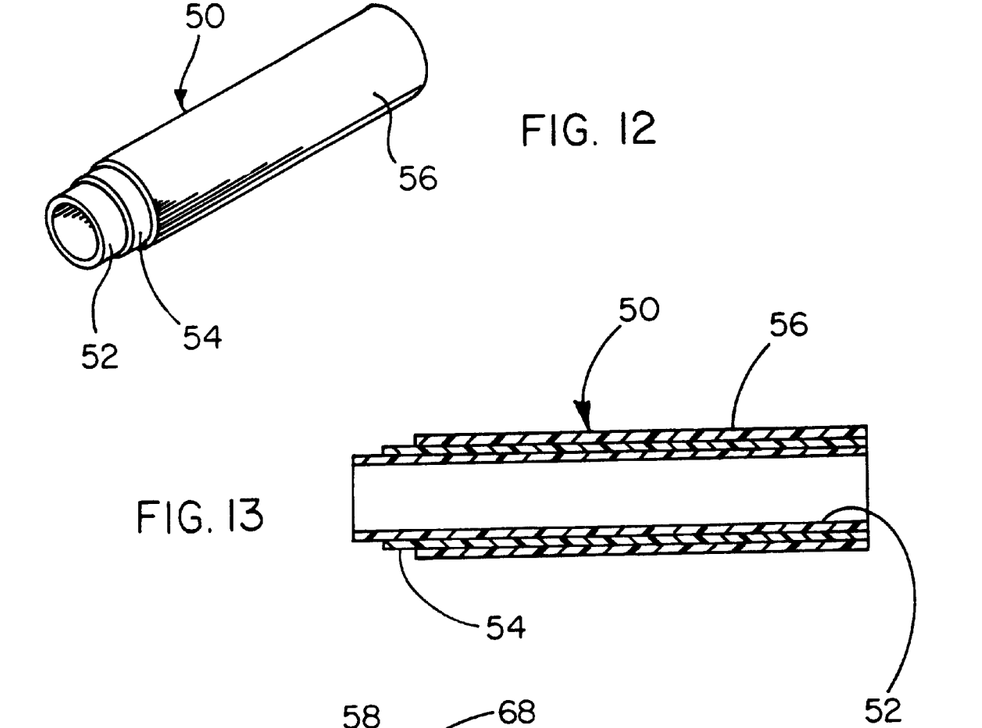
FIG. 12 is a three-quarter isometric view of still another embodiment of a device of the present invention, this embodiment comprising a three layer tubular construction.
FIG. 13 is a longitudinal cross-section of the device of FIG. 12.

Still another embodiment of the present invention is shown in FIGS. 12 and 13. This leak-resistant tube 50 employs three tube elements 52, 54, and 56 connected together with an interference fit. Base tube 52 is surrounded by an intermediate tube 54 that is further covered by an outer tube 56. Tension, compression, or no stress may be applied to one or more of these tube elements to impart a differential stress to the device as a whole. It should be evident that this embodiment allows for event greater misalignment of holes through the device upon removal of a puncture since stresses can be imparted to the device to move each of the layers in different directions during and after a diagonal puncture.

Figures 14, 15:
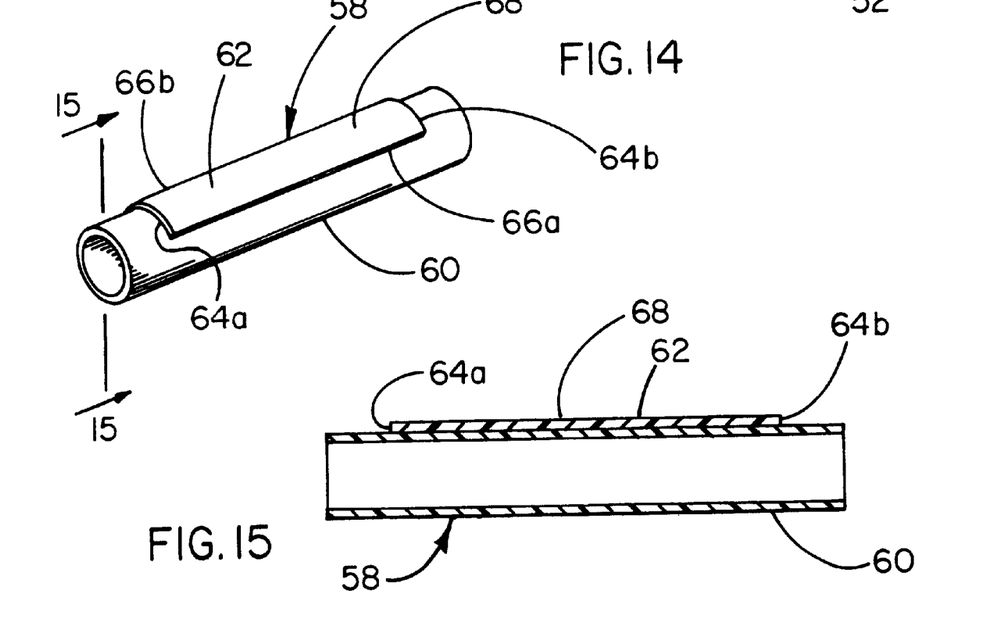
FIG. 14 is a three-quarter isometric view of still another embodiment of a tubular device of the present invention.
FIG. 15 is a cross-section view along line 15—15 of FIG. 14.

FIGS. 14 and 15 illustrate a further embodiment of a vascular graft 58 of the present invention. In this embodiment a first tube element 60 is partially covered with a second element 62 comprising a strip of material. In this form, the second element 62 is anchored to the first tube element 60 on the second element's ends 64a, 64b and perhaps along its longitudinal sides 66a, 66b. In order to function properly, the operative piercing surface 68 of the second element 62 should be free to move relative to the first tube element 60 in order to provide the hole misalignment previously described.

Anchorage between the first tube element 60 and the second element 62 may be accomplished through a variety of means. For example, thin strips of adhesive may be applied near the ends 64a, 64b of the device to anchor the ends in place. Suitable adhesives include fluorinated ethylene propylene (polyurethane, FEP, etc.) Adhesive may also be applied along the sides 66a, 66b. Other anchorage means that may be employed with this embodiment include sutures, staples, clips, etc.

When the second element 62 is constructed from the same material as the first tube element 60 (or constructed from a material with a similar modulus of elasticity as the first tube element 60), it is preferred that a stress differential is applied between the first tube element 60 and the second element 62. This can be accomplished by stretching or compressing the second element 62 before attaching it to the first tube element 60. Alternatively or additionally, the first tube element 60 may be stretched or compressed prior to attachment to establish a stress differential. In addition to a tube or a strip, the second element may also be constructed in a variety of other shapes and sizes. Examples of other configurations include: square, circular, rectangular, or other shaped patches.

Additionally, the second element may be combined in multiple layers and/or in multiple configurations to provide specific properties to the final device. Examples of other constructions include:

In the context of a non-tubular second element, the term "interference fit" is intended to define a snug connection between the first tube element and the second element so that the elements can retain any differential stresses established between them and that the excessive liquid leakage will not occur between the two elements during and after a puncture.

Without intending to limit the scope of the present invention, the following examples illustrate how the present invention may be made and used:

EXAMPLE 1
Leak Resistant Two Layer Tube

A leak-resistant vascular graft of the present invention may be made in the following manner. A commercially available expanded PTFE 6 mm Stretch GORE-TEX® Vascular graft is used for the base graft. This graft has a nominal internal diameter of 6 mm and a nominal wall thickness of 0.60 mm. The base graft is placed onto an assembly mandrel and secured at one end. A load is placed on the opposite end to apply tension to the graft. The thin wall expanded PTFE 6 mm GORE-TEX® graft is used for the outer graft. It has nominal internal diameter of 6 mm and a nominal wall thickness of 0.45 mm. It is pulled over the base graft and the assembly mandrel to create an interference fit between the two grafts. The outer graft is then compressed uniformly along its length to about 60% of its original length. This provides longitudinal compression in the outer graft. The grafts are then removed from the assembly mandrel. In use, longitudinal forces applied to the graft will be applied to the base graft so that the outer graft will remain in compression.

EXAMPLE 2
Ultra Thin Wall Outer Graft

A 6 mm Stretch expanded PTFE GORE-TEX® Vascular graft is used for the base graft. This graft has a nominal internal diameter of 6 mm and a nominal wall thickness of 0.60 mm. The base graft is placed onto an assembly mandrel and secured at one end. A load is placed on the opposite end to apply tension to the graft. An ultra thin wall expanded PTFE 6 mm GORE-TEX® graft is used for the outer graft. It has nominal internal diameter of 6 mm and a nominal wall thickness of 0.25 mm. It is pulled over the base graft and the assembly mandrel creates an interference fit between the two grafts. The outer graft is then compressed uniformly along its length to about 60% of its original length. This provides longitudinal compression in the outer graft. The grafts are then removed from the assembly mandrel. Longitudinal forces applied to the graft will be applied to the base graft so that the outer graft will remain in compression.

EXAMPLE 3
Bonded Grafts

A means can be provided for assuring that the compression in the outer graft is not disturbed during handling and implantation and which still allows the grafts relative motion during cannulation to provide the low leak feature. In this embodiment, a strip of bio-compatible, adhesive material is placed between the grafts. This material is used to bond the two grafts along a narrow strip that is located opposite the side that will be cannulated. This material can be constructed from a number of possible materials, including fluorinated thermoplastics (such as, fluorinated ethylene propylene (FEP) or perfluoroalkoxy polymer (PFA)) as well as silicones and polyurethanes. The material can be applied along a strip as a film or coating. It can also be applied over the entire graft and only be sealed along a narrow strip opposite the cannulation site.

An expanded PTFE 6 mm Stretch GORE-TEX® Vascular graft is used for the base graft. This graft has a nominal internal diameter of 6 mm and a nominal wall thickness of 0.60 mm. A full length and 0.4 cm wide strip of FEP film is applied lengthwise along the graft. The base graft is placed onto an assembly mandrel and secured at one end. A load is placed on the opposite end to apply tension to the graft. A thin wall 6 mm GORE-TEX® graft is used for the outer graft. It has nominal internal diameter of 6 mm and a nominal wall thickness of 0.45 mm. It is pulled over the base graft and the assembly mandrel creating an interference fit between the two grafts. The outer graft is then compressed uniformly along its length to about 60% of its original length. This provides longitudinal compression in the outer graft. Heat and pressure are applied along the outer graft on top of the FEP strip, bonding the two tubes together along a narrow strip opposite the side to be cannulated. The grafts are then removed from the assembly mandrel. Longitudinal forces applied to the graft will be applied to the base graft so that the outer graft will remain in compression. The two tubes are able to displace during cannulation along the cannulation side, but the compression of the outer tube is resistant to change during handling and implantation

EXAMPLE 4

Additional tubes of varying thickness, density and structural orientation can be combined to further maximize hole misalignment and/or hole healing effects, as is illustrated in FIGS. 12 and 13, as previously described.

For example, a base tube of an expanded PTFE 6 mm Stretch GORE-TEX® Vascular graft is positioned on a vacuum mandrel in a longitudinally relaxed state. Vacuum is applied to the mandrel, collapsing the outer diameter (OD) of the graft. An ultra thin wall expanded PTFE 6 mm GORE-TEX® graft is positioned on top of the base graft in a fully distended condition. A second ultra thin wall 6 mm GORE-TEX® graft is positioned over the first two grafts and compressed uniformly along its length to about 60% of its original length. The grafts are then removed from the vacuum mandrel. The graft provides a middle layer that bears all axial loads, a neutrally loaded inner layer that is easily displaced relative to the other two layers by penetration forces, and an outer layer that is compressively loaded to provide a healing effect.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A tube resistant to leakage when punctured comprising
   a first tube element having a length;
   a second element having a length;
   the second element placed over the first tube element with an interference fit between the first tube element and the second element;
   wherein the first tube element and second element are adapted to move relative to one another when a diagonal puncture is place through the tube with a needle creating a misalignment of a hole through the first tube element and a hole in the second element when the needle is removed;
   wherein when in an interference fit between the first tube element and the second element, the first tube element has a stress applied along its length different from a stress applied to the second element along its length; and
   wherein the first tube element and the second element each has a natural resting state of stress along its length; and the first tube element is stretched from its natural state of stress and the second element is compressed from its natural state of stress.

2. The tube of claim 1 wherein the tube is adapted to used as a vascular graft and is constructed from materials suitable for implantation.

3. The first tube of claim 2 wherein the tube element comprises polytetrafluoroethylene.

4. The first tube of claim 3 wherein the tube element comprises expanded polytetrafluoroethylene.

5. The tube of claim 1 wherein the second element comprises at least one strip of material attached to the first tube element.

6. The tube of claim 1 wherein the tube includes a third tube element.

7. A tube resistant to leakage when punctured comprising
   a first tube element having a longitudinal axis and a length;
   a second tube element having a longitudinal axis and a length;
   the second tube element attached coaxially to the first tube element;
   the combination of the first tube element and the second tube element being adapted so that the second tube element bears no tensile load when the first tube element is distended under pressure.

8. The tube of claim 7 wherein the tube is adapted to be used as a vascular graft and is constructed from material suitable for implantation.

9. The tube of claim 7 wherein the first and second tube elements are adapted to move relative to one another when a puncture is placed through the tube with a needle.

10. The tube of claim 7 wherein the first tube element and the second tube element have an interference fit between them.

11. The tube of claim 7 wherein the first tube element and the second tube element are adapted to move relative to one another when a diagonal puncture is placed through the tube.

12. A tube resistant to leakage when punctured comprising
   a first tube element having a length;
   a second element having a length;
   the second element placed over the first tube element with an interference fit between the first tube element and the second element;
   wherein the first tube element and second element are adapted to move relative to one another when a diagonal puncture is place through the tube with a needle creating a misalignment of a hole through the first tube element and a hole in the second element when the needle is removed;
   wherein when in an interference fit between the first tube element and the second element, the first tube element has a stress applied along its length different from a stress applied to the second element along its length; and
   wherein the first tube element and the second tube element each has a natural resting state of stress along its length; and the second element is stretched from its natural state of stress and the first tube element is compressed from its natural state of stress.

13. A tube resistant to leakage when punctured comprising
   a first tube element having a length;
   a second element having a length;
   the second element placed over the first tube element with an interference fit between the first tube element and the second element;
   wherein the first tube element and second element are adapted to move relative to one another when a diagonal puncture is place through the tube with a needle creating a misalignment of a hole through the first tube element and a hole in the second element when the needle is removed;
   wherein the second element comprises a tubular element;
   wherein when in an interference fit between the first tube element and the second element, the first tube element has a stress applied along its length different from a stress applied to the second element along its length; and wherein the first tube element and the second element each has a natural resting state of stress along its length; and the first tube element is stretched from its natural state of stress and the second element is compressed from its natural state of stress.

14. A tube resistant to leakage when punctured comprising a first tube element having a length;

a second element having a length;

the second element placed over the first tube element with an interference fit between the first tube element and the second element;

wherein the first tube element and second element are adapted to move relative to one another when a diagonal puncture is place through the tube with a needle creating a misalignment of a hole through the first tube element and a hole in the second element when the needle is removed, wherein the second element comprises a tubular element;

wherein when in an interference fit between the first tube element and the second element, the first tube element has a stress applied along its length different from a stress applied to the second element along its length; and wherein the first tube element and the second tube element each has a natural resting state of stress along its length; and the second element is stretched from its natural state of stress and the first tube element is compressed from its natural state of stress.

15. A tube resistant to leakage when punctured comprising a first tube element having a length;

a second element having a length;

the second element placed over the first tube element with an interference fit between the first tube element and the second element;

wherein the first tube element and second element are adapted to move relative to one another when a diagonal puncture is place through the tube with a needle creating a misalignment of a hole through the first tube element and a hole in the second element when the needle is removed; and wherein the second element comprises at least one strip of material attached to the first tube element.

16. The tube of claim 15 wherein when in an interference fit between the first tube element and the second element, the first tube element has a stress applied along its length different from a stress applied to the second element along its length.

17. The tube of claim 16 wherein the first tube element and the second element each has a natural resting state of stress along its length; and the second element is stretched from its natural state of stress and the first tube element is compressed from its natural state of stress.

18. The tube of claim 15 wherein the second element comprises a tubular element.

19. The tube of claim 18 wherein when in an interference fit between the first tube element and the second element, the first tube element has a stress applied along its length different from a stress applied to the second element along its length.

20. The tube of claim 9 wherein the first tube element and the second element each has a natural resting state of stress along its length; and the first tube element is stretched from its natural state of stress and the second element is compressed from its natural state of stress.

21. The tube of claim 19 wherein the first tube element and the second tube element each has a natural resting state of stress along its length; and the second element is stretched from its natural state of stress and the first tube element is compressed from its natural state of stress.

22. The tube of claim 18 wherein the first tube element has an inside diameter and an outside diameter;

the second element has an inside diameter and an outside diameter; and the inside diameter of the second element is less than or equal to the outside diameter of the first tube element.

23. A tube resistant to leakage when punctured comprising a first tube element having a length;

a second element having a length;

the second element placed over the first tube element with an interference fit between the first tube element and the second element, wherein the first tube element and second element are adapted to move relative to one another when a diagonal puncture is place through the tube with a needle creating a misalignment of a hole through the first tube element and a hole in the second element when the needle is removed; and wherein the tube includes a third tube element.

* * * * *